United States Patent
Ohmori et al.

(10) Patent No.: US 6,607,736 B2
(45) Date of Patent: Aug. 19, 2003

(54) SKIN PREPARATIONS FOR EXTERNAL USE

(75) Inventors: Takashi Ohmori, Yokohama (JP); Reiji Miyahara, Yokohama (JP); Hiroyuki Kakoki, Yokohama (JP); Tomiyuki Namba, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 09/890,285

(22) PCT Filed: Dec. 19, 2000

(86) PCT No.: PCT/JP00/08982
§ 371 (c)(1),
(2), (4) Date: Aug. 13, 2001

(87) PCT Pub. No.: WO01/45665
PCT Pub. Date: Jun. 28, 2001

(65) Prior Publication Data
US 2003/0091603 A1 May 15, 2003

(30) Foreign Application Priority Data

Dec. 20, 1999 (JP) .......................... 11-360818
Jan. 26, 2000 (JP) ....................... 2000-017423
Aug. 7, 2000 (JP) ....................... 2000-238126

(51) Int. Cl.$^7$ .............. A61K 6/00; A61K 7/00
(52) U.S. Cl. ................. 424/401; 424/62; 514/547; 514/844; 514/474
(58) Field of Search ............ 424/401, 62; 514/547, 514/844, 474

(56) References Cited

U.S. PATENT DOCUMENTS

| 5,238,678 A | | 8/1993 | Nakamura | |
|---|---|---|---|---|
| 5,427,775 A | * | 6/1995 | Sakai et al. | 424/62 |
| 5,437,860 A | * | 8/1995 | Jarvis et al. | 424/70.2 |
| 5,767,158 A | * | 6/1998 | Suetsugu et al. | 514/563 |
| 5,962,524 A | * | 10/1999 | Rodelet | 514/547 |
| 5,993,793 A | | 11/1999 | Bollens et al. | |

FOREIGN PATENT DOCUMENTS

| EP | 0561305 A | 9/1993 |
|---|---|---|
| EP | 0904772 A | 9/1993 |
| EP | 0591546 A | 4/1994 |
| EP | 1129686 A | 9/2001 |
| JP | 55-17310 | * 6/1980 |
| WO | WO9500107 A | 1/1995 |

OTHER PUBLICATIONS

Kunishige et al. JP 55–17310 (1980), Abstract.*
PTO 2002–0840, Method to Manufacture External Medicines, English translation of JP 55–017310 (Feb. 1980).*
Database CA 'Online!, XP002218837 & Abstract & JP 55 017310 A.
Database CA 'Online!, XP002218838 & Abstract & Eisei Kagaku (1989).

* cited by examiner

Primary Examiner—Sreeni Padmanabhan
Assistant Examiner—Gina C. Yu
(74) Attorney, Agent, or Firm—Townsend & Banta

(57) ABSTRACT

An endermic liniment comprising a polyoxyethylene dicarboxylate represented by the following chemical formula (1).

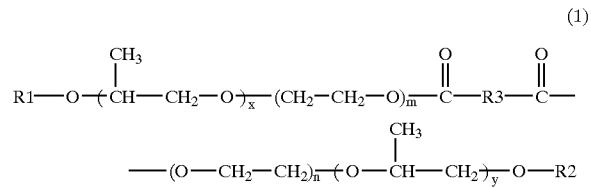

(In this formula, R1 and R2 are hydrogen or alkyl or branched alkyl groups having 1–4 carbon atoms, and m, n, X, and Y are integers 0–5 which are not all zero at the same time. R3 is a branched or linear chain alkylene group having 0–10 carbon atoms.)

The endermic liniment of the present invention achieves superior tactile sensation during use, smoothness in particular, without a sticky sensation, while maintaining a lasting moisture retaining effect by means of blending in a humectant and a polyoxyethylene dicarboxylate.

3 Claims, No Drawings

SKIN PREPARATIONS FOR EXTERNAL USE

TECHNICAL FIELD

The present invention relates to an endermic liniment comprising a polyoxyethylene dicarboxylate. The present invention also relates to a whitening endermic liniment with superior tactile sensation during use.

BACKGROUND ART

Retention of moisture is essential for maintaining healthy skin, and many endermic liniments designed for moisture retention have been developed. As far as the sensation at the time of application of an endermic liniment is concerned, smoothness without a sticky sensation is desired.

Research with regard to humectants is carried out intensively; humectants such as organic salts, polyhydric alcohols, and water-soluble polymers are blended in an endermic liniment today.

However, the blend ratio of these humectants must be increased in order to increase the moisture retaining effect, and as a result there are the following problems to be solved: the system becomes unstable, usability becomes poor, and, when applied to skin, it is repelled by sebum, or fitness for skin becomes poor.

The inventors conducted earnest research in view of the aforementioned problems and discovered that an endermic liniment that is superior in terms of the tactile sensation during use, smoothness in particular, without a sticky sensation, and having a lasting moisture retaining effect, can be obtained when a polyoxyethylene dicarboxylate and a humectant are blended in an endermic liniment, thus completing the present invention.

The object of the present invention is to provide an endermic liniment comprising a polyoxyethylene dicarboxylate which promotes the effect of the ingredients, and in particular to provide an endermic liniment comprising a humectant in combination with the polyoxyethylene dicarboxylate.

The mechanism of the development of skin stains and such is somewhat unclear, but it is generally believed that hormone anomalies and/or the stimulus of ultraviolet light from the sun causes melanin formation, which abnormally deposits in the skin.

For a means to improve such stains and birthmarks, a method is known in which a substance controlling the production of melanin, such as L-ascorbic acid and its derivative, glucoside of hydroquinone and its derivative, kojic acid and its derivative as described in, for example, Japanese Patent Unexamined Publication No. H09-263514 bulletin, is added to a cosmetic.

However, although the aforementioned method has superior whitening effect and the effect of reducing skin irritation, it has a problem in usability because of a tendency to give a sticky sensation during use, a lack of smoothness after application to the skin, etc. Therefore, there is a problem to be solved in that consumers stay away from the products.

The inventors conducted earnest research in view of the aforementioned problem and discovered that an endermic liniment which maintains the whitening effect and yet is superior in terms of tactile sensation, smoothness in particular, during use, and no stickiness can be obtained by blending a polyoxyethylene dicarboxylate in an endermic liniment containing L-ascorbic acid or its derivative, a glucoside of hydroquinone or its derivative, and kojic acid or its derivative, and thus completed the present invention.

The object of the present invention is to provide an endermic liniment containing L-ascorbic acid or its derivative, a glucoside of hydroquinone or its derivative, and kojic acid or its derivative which offers superior tactile sensation without sacrificing the whitening effect.

DISCLOSURE OF INVENTION

That is, the present invention provides an endermic liniment which contains a polyoxyethylene dicarboxylate represented by the following chemical formula (1):

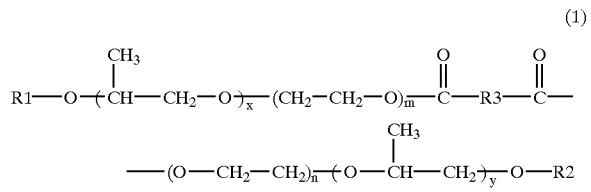

(1)

(In this formula, R1 and R2 are hydrogen or alkyl or branched alkyl groups having 1–4 carbon atoms, and m, n, X, and Y are integers 0–5 which are not all zero at the same time. R3 is a branched or linear chain alkylene group having 0–10 carbon atoms.)

Also, the present invention provides said endermic liniment wherein said polyoxyethylene dicarboxylate is diethoxy ethyl succinate.

Furthermore, the present invention provides said endermic liniment containing a humectant.

That is, the present invention provides an endermic liniment comprising a polyoxyethylene dicarboxylate which is represented by the following chemical formula (1), as well as one, two or more compounds selected from the group consisting of L-ascorbic acid or its derivative, a glucoside of hydroquinone or its derivative, and kojic acid or its derivative.

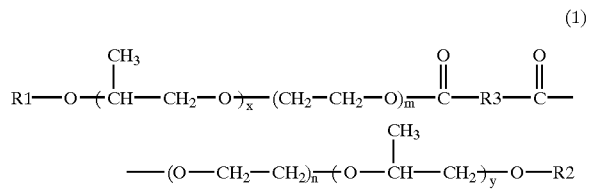

(1)

(In this formula, R1 and R2 are hydrogen or alkyl or branched alkyl groups having 1–4 carbon atoms, and m, n, X, and Y are integers 0–5 which are not all zero at the same time. R3 is a branched or linear chain alkylene group having 0–10 carbon atoms.)

Also, the present invention provides said endermic liniment wherein said polyoxyethylene dicarboxylate is diethoxy ethyl succinate.

Furthermore, the present invention provides said endermic liniment containing a humectant.

Also, the present invention provides said endermic liniment wherein said endermic liniment is a whitening endermic liniment.

BEST MODE FOR CARRYING OUT THE INVENTION

The configuration of the present invention is described in detail below.

Polyoxyethylene dicarboxylates of the aforementioned chemical formula used in the present invention (1) are known substances, but are new as an endermic liniment ingredient.

In chemical formula (1), R1 and R2 denote alkyl or branched alkyl groups with a carbon number of 1–4; when the carbon number exceeds 5, hydrophilicity is reduced and the stability of the system becomes poor as they are blended in an endermic liniment (lotion in particular). m, n, X, and Y denote an integer of 0–5. Preferably they should be integers 1–2. If the total of m, n, X, and Y is zero, then hydrophilicity is reduced and the stability of the system becomes poor as they are blended in an endermic liniment (lotion in particular). If it is more than 15, then the tactile sensation during use, smoothness in particular, becomes insufficient. R3 denote an alkyl or branched alkyl group with a carbon number of 0–10; when the carbon number exceeds 10, hydrophilicity is reduced and the stability of the system becomes poor as it is blended in an endermic liniment (lotion in particular).

Of polyoxyethylene dicarboxylates (1), diethoxyethyl succinate is preferably used due to its tactile sensation during use. An endermic liniment with particularly superior smoothness and without a sticky sensation which has a lasting moisture effect can be obtained.

The blend ratio of the polyoxyethylene dicarboxylate is not limited in particular, but preferably 0.001–20.0 wt %, more preferably 0.1–10.0 wt % based upon the total amount of the endermic liniment. If it is less than 0.001 wt %, then the effect of the blending is not manifested. If it is over 20.0 wt %, then a sticky sensation will arise after use.

Examples of the humectant used in the present invention include polyethylene glycol, propylene glycol, glycerin, 1,3-butylene glycol, xylitol, sorbitol, maltitol, chondroitin sulfate, hyaluronic acid, mucoitin sulfuric acid, charonic acid, atelocollagen, cholesteryl-12-hydroxy stearate, sodium lactate, bile salt, dl-pyrrolidone carboxylic acid salt, short chain soluble collagen, diglycerin (EO)PO adduct, chestnut rose extract, yarrow extract, and sweet clover extract.

The blend ratio of the humectant is not limited in particular; it is preferably 0.001–20.0 wt %, more preferably 0.1–10.0 wt %, based upon the total amount of the endermic liniment.

Invention Defined in Claims 4–7

Polyoxyethylene dicarboxylates of the aforementioned chemical formula used in the present invention (1) are known substances, but are new as an endermic liniment ingredient.

In chemical formula (1), R1 and R2 denote alkyl or branched alkyl groups with a carbon number of 1–4; when the carbon number exceeds 5, hydrophilicity is reduced and the stability of the system becomes poor as they are blended in an endermic liniment (lotion in particular). m, n, X, and Y denote an integer of 0–5. Preferably they should be integers 1–2. If the total of m, n, X, and Y is zero, then hydrophilicity is reduced and the stability of the system becomes poor as they are blended in an endermic liniment (lotion in particular). If it is more than 15, then the tactile sensation during use, smoothness in particular, becomes insufficient. R3 denotes an alkyl or branched alkyl group with a carbon number of 0–10; when the carbon number exceeds 10, hydrophilicity is reduced and the stability of the system becomes poor as it is blended in an endermic liniment (lotion in particular).

Of polyoxyethylene dicarboxylates (1), diethoxyethyl succinate is preferably used due to its tactile sensation during use. An endermic liniment that is superior in terms of the tactile sensation during use, smoothness in particular, and without a sticky sensation is obtained while maintaining the whitening effect.

The blend ratio of the polyoxyethylene dicarboxylate is not limited in particular, but preferably 0.001–20.0 wt %, more preferably 0.1–10.0 wt %, based upon the total amount of the endermic liniment. If it is less than 0.001 wt % then the effect of the blending is not achieved. If it is over 20.0 wt % then a sticky sensation will arise after use.

L-Ascorbic acid used in the present invention is generally called vitamin C; due to its strong reducing function, it has a cellular respiration action, enzyme activation action, collagen formation action, as well as the melanin reducing action. Examples of the L-ascorbyl derivative include L-ascorbyl alkyl ester, L-ascorbyl phosphate, and L-ascorbyl sulfate. Specific examples include L-ascorbyl alkylether such as L-ascorbyl palmitatel, L-ascorbyl isopalmitate, L-ascorbyl dipalmitate, L-ascorbyl diisopalmitate, L-ascorbyl stearate, L-ascorbyl isostearate, L-ascorbyl distearate, L-ascorbyl diisostearate, L-ascorbyl myristate, L-ascorbyl isomyristate, L-ascorbyl dimyristate, L-ascorbyl diisomyristate, L-ascorbyl 2-ethylhexanoate, L-ascorbyl di2-ethylhexanoate, L-ascorbyl oleate, and L-ascorbyl dioleate; L-ascorbyl phosphate such as L-ascorbyl-2-phosphate, L-ascorbyl-3-phosphate, and DL-α-tocopherol-2-L-phosphate ascorbate; and L-ascrobyl sulfate such as L-ascorbyl-2-sulfate and L-ascorbyl-3-sulfate. In addition, a salt of these cans be used as well; alkali metal salts such as sodium salts and potassium salts, alkaline earth metal salts such as calcium salts and magnesium salts, etc. are preferably used. The aforementioned L-ascorbic acid or its derivative is obtained by a known synthesis, but, of course those obtained by other methods can also be used; commercially available derivatives of vitamin C can be used.

Examples of the kojic acid detivative used in the present invention include kojic esters such as kojic alkyl ester and kojic ethers such as kojic alkyl ether.

The glucoside of hydroquinone used in the present invention includes hexose glucosides such as hydroquinone α-D-glucose, hydroquinone β-D-glucose, hydroquinone α-L-glucose, hydroquinone β-L-glucose, hydroquinone α-D-galactose, hydroquinone β-D-galactose, hydroquinone α-L-galactose, and hydroquinone β-L-galactose; pentose glucoside such as hydroquinone α-D-ribose, hydroquinone β-D-ribose, hydroquinone α-L-ribose, hydroquinone β-L-ribose, hydroquinone α-D-arabinose, hydroquinone β-D-arabinose, hydroquinone α-L-arabinose, and hydroquinone β-L-arabinose: amino acid glucosides such as hydroquinone α-D-glucosamine, hydroquinone β-D-glucosamine, hydroquinone α-L-glucosamine, hydroquinone β-L-glucosamine, hydroquinone α-D-galactosamine, hydroquinone β-D-galactosamine, hydroquinone α-L-galactosamine, and hydroquirione β-L-galactosamine; uronic acid glucosides such as hydroquinone α-D-glucuronic acid, hydroquinone β-D-glucuronic acid, hydroquinone α-L-glucuronic acid, hydroquinone β-L-glucuronic acid, hydroquinone α-D-galacturonic acid, hydroquinone β-D-galacturonic acid, hydroquinone α-L-galacturonic acid, and hydroquinone β-L-galacturonic acid. Examples of their derivatives include esters such as acetylated derivatives and ethers such as methylated derivatives. Of these, hydroquinone β-D-glucose is desirable in view of the whitening effect, availability, and stability.

Of the aforementioned L-ascorbic acid or its derivative, a glucoside of hydroquinone or its derivative, and kojic acid or its derivative, one, two or more can be selected at will. The blend ratio is not limited in particular; it is preferably 0.001–15.0 mass %, more preferably 0.1–10.0 mass %, based upon the total amount of the endermic liniment.

In the present invention, it is preferable to additionally blend in a humectant. Examples of the humectant include polyethylene glycol, propylene glycol, glycerol, 1,3-butylene glycol, xylitol, sorbitol, maltitol, chondroitin sulfate, hyaluronic acid, mucoitin sulfuric acid, charonic acid, atelocollagen, cholesteryl-12-hydroxy stearate, sodium lactate, bile salt, dl-pyrrolidone carboxylic acid salt, short chain soluble collagen, diglycerin (EO)PO adduct, cheastnut rose extract, yarrow extract, and sweet clover extract.

The blend ratio of the humectant is not limited in particular; it is preferably 0.001–20.0 mass %, more preferably 0.1–10.0 mass %, based upon the total amount of the endermic liniment.

Common Description

The endermic liniment of the present invention is prepared by blending the aforementioned essential ingredients in an existing endermic liniment base. In addition to the aforementioned essential ingredients, other ingredients used in endermic liniments such as cosmetics and drugs can be blended as necessary in the endermic liniment of the present invention; examples of such ingredients include powder ingredients, liquid fats and oils, solid fats and oils, waxes, hydrocarbons, higher fatty acids, higher alcohols, esters, silicones, anionic surfactants, cationic surfactants, ampholytic surfactants, nonionic surfactants, humectants, water-soluble polymers, thickeners, coating agents, ultraviolet light absorbents, sequestering agents, lower alcohols, polyhydric alcohols, sugars, amino acids, organic amines, polymer emulsions, pH adjusting agents, skin nutrients, vitamins, antioxidants, antioxidation assistants, perfumes, and water; and the endermic liniment can be prepared for the target formulation with a conventional method. Specific ingredients which can be blended in are listed below. The endermic liniment of the present invention can be prepared by blending the aforementioned essential ingredients and any one, two or more of the following ingredients.

Examples of the powder ingredients include inorganic powders (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, firing calcium sulfate (calcined gypsum), calcium phosphate, fluorineapatite, hydroxy apatite, ceramic powder, metallic soaps (for example, myristic acid zinc, calcium palmitate, and aluminum stearate), and boron nitride); organic powders (for example, polyamide resin powder (nylon powder), polyethylene powder, poly methyl methacrylate powder, polystyrene powder, powders of copolymer resin of styrene and acrylic acid, benzoguanamine resin powder, polytetrafluoroethylene powder, and cellulose powder); inorganic white pigments (for example, titanium dioxide and zinc oxide); inorganic red pigments (for example, iron oxide (red iron oxide) and iron titanate); inorganic brown pigments (for example, γ-iron oxide); inorganic yellow pigments (for example, yellow iron oxide and loess); inorganic black pigments (for example, black iron oxide and low oxides of titanium); inorganic purple pigments (for example, mango violet, cobalt violet); inorganic green pigments (for example, chromium oxide, chromium hydroxide, and cobalt titanate); inorganic blue pigments (for example, ultramarine blue and Berlin blue); pearl pigment (for example, titania coated mica, titania coated bismuth oxychloride, titania coated talc, coloration titania coated mica, bismuth oxychloride, fish scale flakes); metal powder pigments (for example, aluminium powder, copper powder); organic pigments such as Zr, barium or aluminium rake (for example, organic pigments such as red 201, red 202, red 204, red 205, red 220, red 226, red 228, red 405, orange 203, orange 204, yellow 205, yellow 401 and blue 404, as well as red 3, red 104, red 106, red 227, red 230, red 401, red 505, orange 205, yellow 4, yellow 5, yellow 202, yellow 203, green 3 and blue 1); and natural colors (for example, chlorophyll and β-carotene).

Examples of the liquid fats and oils include avocado oil, tsubaki oil, turtle fatty acid, macademia nut oil, corn oil, mink oil, olive oil, rape oil, egg yolk oil, sesame oil, persic oil, wheat germ oil, sasanqua oil, castor oil, linseed oil, safflower oil, cotton seed oil, perilla oil, soybean oil, peanut oil, tea seed oil, Japanese nutmeg oil, rice bran oil, Chinese gimlet oil, Japan gimlet oil, jojoba oil, germ oil, and triglycerin.

Examples of the solid fats and oils include cacao butter, coconut oil, horse fat, hydrogenated coconut oil, palm oil, beef tallow, mutton tallow, hydrogenated beef tallow, palm kernel oil, lard, beef bone fat, Japanese core wax nucleus oil, hydrogenated oil, neatsfoot oil, Japanese core wax, and hydrogenated castor oil.

Examples of the waxes include beeswax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin ethyl alcohol ether.

Examples of the hydrocarbon oils include liquid petrolatum, ozocerite, squalane, pristane, paraffin, ceresin, squalene, and petrolatum, and microcrystallin wax.

Examples of the higher fatty acids include lauric acid, myristic acid, palmitic acid, stearic acid, behenic acid, oleic acid, undecylenic acid, tall oil, isostearic acid, linolic acid, linoleic acid, eicosapentaenoic acid (EPA), and docosahexaenoic acid (DHA).

Examples of the higher alcohols include straightchain alcohol (for example, lauryl alcohol, cetyl alcohol, stearyl alcohol, behenyl alcohol, myristyl alcohol, oleyl alcohol, and cetostearyl alcohol) and branched chain ethyl alcohol (for example, mono stearyl glycerin ether (batyl alcohol), 2-decyltetradecynol, lanolin alcohol, cholesterol, phytosterol, hexyl dodecanol, iso stearyl alcohol, and octyl dodecanol).

Examples of the synthesized ester oils include isopropyl myristate, cetyl octanoate, octyl dodecyl myristate, isopropyl palmitate, butyl stearate, hexyl laurate, myristil myristate, decyl oleate, dimethyl hexyl decyl octanoate, cetyl lactate, myristil lactate, lanolin acetate, iso cetyl stearate, iso cetyl isostearate, cholesteryl hydroxy 12-stearate, di-2-ethylene glycol ethylhexanoate, dipentaerythritol fatty acid ester, n-alkylene glycol monoisostearate, neopentyl glycol dicaprate, diisostearyl malate, glyceryl di-2-heptylundecanoate, trimethylolpropane tri-2-ethylhexanoate, trimethylolpropane triisostearate, tetra-2-pentaerythritol ethylhexanoate, glycerin tri-2-ethylhexanoate, glyceryl trioctanoate, glycerin triisopalmitate, trimethylolpropane triisostearate, cetyl 2-ethyl hexanoate, 2-ethylhexyl palmitate, glycerin trimyristate, tri-2-heptyl undecanoate glyceride, methyl castor oil fatty acid, oleyl oleate, aceto glyceride, 2-heptyl undecyl palmitate, diisobutyl adipate, 2-octyldodecyl N-lauroyl-L-glutamate, di-2-heptyl undecyl adipate, ethyl laurate, di-2-ethylhexyl sebacate, 2-hexyl decyl myristate, 2-hexyl decyl palmitate, 2-hexyl decyl adipate, diisopropyl sebacate, 2-ethylhexyl succinate, and triethyl citrate.

Examples of the silicone oils include chain polysiloxanes (for example, dimethylpolysiloxane, methylphenyl polysiloxane, and diphenyl polysiloxane); cyclic polysiloxanes (for example, octamethylcyclotetrasiloxane, decamethyl cyclopenta siloxane, and dodecamethyl cyclohexa siloxane), silicone resins forming a three-dimensional network structure, silicone rubbers, and various modified polysiloxanes (amino-modified polysiloxane, polyether-modified polysiloxane, alkyl-modified polysiloxane, and fluorine-modified polysiloxane).

Examples of the anionic surfactants include fatty acid soaps (for example, sodium laurate and sodium palmitate); higher alkyl sulfuric ester salts (for example, sodium lauryl sulfate and potassium laurylsulfate); alkylether sulfuric ester salts (for example, POE-triethanolamine laurylsulfate, sodium POE-lauryl sulfate); N-acyl sarcosinic acids (for example, sodium N-lauroyl sarcosinate); higher fatty acid amidosulfonic acid salts (for example, sodium N-myristoyl-N-methyl taurate, sodium N-cocoyl N-methyl taurate, and sodium lauryl methyl taurate); phosphate salts (sodium POE-oleyl ether phosphate, POE-stearyl ether phosphoric acid, etc.); sulfosuccinates (for example, sodium di-2-ethylhexylsulfosuccinate, sodium mono lauroyl mono ethanol amide polyoxyethylene sulfosuccinate, and sodium lauryl polypropylene glycol sulfosuccinate); alkylbenzene sulfonates (for example, sodium linear dodecylbenzenesulfonate, triethanolamine linear dodecylbenzenesulfonate, and linear dodecylbenzene-sulfonic acid); higher fatty acid ester sulfates (for example, hydrogenated palm oil fatty acid glycerine sodium sulfate): N-acyl glutamates (for example, mono sodium N-lauroylglutamate, disodium N-stearoylglutamate, and sodium N-myristoyl-L-glutamate); sulfated oils (for example, turkey red oil); POE-alkylether carboxylic acid; POE-alkylaryl ether carboxylate; α-olefin sulfonate; higher fatty acid ester sulfonates; sec-alcohol sulfates; higher fatty acid alkyl amide sulfates; sodium lauroyl monoethanolamine succinates; and ditriethanolamine N-palmitoylaspartate; and sodium caseinate.

Examples of the cationic surfactants include alkyltrimethylammonium salts (for example, stearyltrimethyl ammonium chloride and lauryltrimethyl ammonium chloride); alkylpyridinium salts (for example, cetylpyridinium chloride); distearyldimethylammonium dialkyldimethylammonium chloride; poly (N,N'-dimethyl-3,5-methylene piperidinium) chloride; alkyl quaternary ammonium salts; alkyl dimethylbenzyl ammonium salts; alkyl isoquinolinium salts; dialkylmorpholine salts; POE-alkylamines; alkylamine salts; polyamine fatty acid derivatives; amylalcohol fatty acid derivatives; benzalkonium chloride; and benzethonium chloride.

Examples of the ampholytic surfactants include: imidazoline type ampholytic surfactants (for example, 2-undecyl-N,N,N-(hydroxyethyl carboxymethyl)-2-imidazoline sodium salt and 2-coco yl-2-imidazolinium hydroxide-1-carboxyethyloxy 2 sodium salt); betaine type surtactants (for example, 2-heptadecyl-n-carboxymethyl-n-hydroxyethyl imidazolinium betaine, lauryldimethylamino betaine acetate, alkyl betaine, amide betaine, and sulfobetaine).

Examples of the lipophilic nonionic surface active agent include sorbitan fatty acid esters (for example, sorbitan mono oleate, sorbitan mono isostearate, sorbitan mono laurate, sorbitan mono palmitate, sorbitan mono stearate, sorbitan sesqui oleate, sorbitan trioleate, diglycerol sorbitan penta-2-ethylhexylate, diglycerol sorbitan tetra-2-ethylhexylate); glycerin polyglycerin aliphatic acids (for example, mono cottonseed oil fatty acid glycerine, glyceryl monoerucate, glycerin sesquioleate, glyceryl monostearate, α,α'-glyceryl oleate pyroglutamate, monostearate glycerine malic acid); propylene glycol fatty acid esters (for example, propylene glycol monostearate); hydrogenated castor oil derivatives; and glycerin alkylethers.

Examples of the hydrophilicity nonionic surface active agents include: POE-sorbitan fatty acid esters (for example, POE-sorbitan monooleate, POE-sorbitan monostearate, POE-sorbitan monoolate, and POE-sorbitan tetraoleate); POE sorbitol fatty acid esters (for example, POE sorbitol monolaurate, POE-sorbitol monooleate, POE-sorbitolpentaoleate, and POE-sorbitol monostearate); POE-glycerin fatty acid esters (for example, POE-monooleate such as POE-glycerin monostearate, POE-glycerin monoisostearate, and POE-glycerin triisostearate); POE-fatty acid esters (for example, POE-distearate, POE-monodioleate, and ethylene glycol distearate); POE-alkylethers (for example, POE-lauryl ether, POE-oleyl ether, POE-stearyl ether, POE-behenyl ether, POE-2-octyl dodecyl ether, and POE-cholestanol ether); pluaronic types (for example, pluaronic); POE/POP-alkylethers (for example, POE/POP-cetyl ether, POE/POP-2-decyl tetradecyl ether, POE/POP-monobutyl ether, POE/POP-lanolin hydrate, and POE/POP-glycerin ether); tetra POE/tetra POP-diaminoethane condensates (for example, tetronic); POE-castor oil hydrogenated castor oil derivatives (for example, POE-castor oil, POE-hydrogenated castor oil, POE-hydrogenated castor oil monoisostearate, POE-hydrogenated castor oil triisostearate, POE-hydrogenated castor oil monopyroglutamic monoisostearic diester, and POE-hydrogenated castor oil maleic acid); POE-beeswax/lanolin derivatives (for example, POE-sorbitol beeswax); alkanol amides (for example, coconut fatty acid diethanol amide, laurate monoethanolamide, and aliphatic acid isopropanol amide); POE-propylene glycol fatty acid esters; POE-alkylamines; POE-aliphatic acid amides; sucrose fatty acid estesr; alkyl ethoxy dimethylamine oxides; and trioleyl phosphoric acid.

Examples of the natural water-soluble polymer include: plant-type polymers (for example, gum arabic, gum tragacanth, galactan, guar gum, carob gum, karaya gum, carrageenan, pectin, agar, quince seed (*Cydonia oblonga*), algae colloids (brown algae extract), starches (rice, corn, potate, and wheat), and glycyrrhizic acid); microorganism-type polymers (for example, xanthan gum, dextran, succinoglucan, and pullulan); and animal-type polymers (for example, collagen, casein, albumin, and gelatin).

Examples of the semisynthetic water-soluble polymers include: starch-type polymers (for example, carboxymethyl starch and methylhydroxypropyl starch); cellulosic polymers (for example, methyl cellulose, ethyl cellulose, methylhydroxypropyl cellulose, hydroxyethyl cellulose, cellulose sodium sulfate, hydroxypropyl cellulose, carboxymetyl-cellulose, sodium carboxymethyl cellulose, crystal cellulose, and cellulose powder); and alginic acid-type polymers (for example, sodium alginate and propyleneglycol alginate).

Examples of the synthetic water-soluble polymers include; vinyl polymers (for example, polyvinyl alcohol, polyvinyl methyl ether, polyvinylpyrrolidone, carboxy vinyl polymer); polyoxyethylene-type polymers (for example, a copolymer of polyethylene glycol 20,000, 40,000, or 60,000 and polyoxyethylene polyoxypropylene); acrylic polymers (for example, sodium polyacrylate, polyethylacrylate, and polyacrylamide); polyethyleneimine; and cationic polymers.

Examples of the thickeners include: gum arabic, carrageenan, karaya gum, gum tragacanth, carob gum, quince seed (*Cydonia oblonga*), casein, dextrin, gelatin, sodium pectate, sodium alginate, methyl cellulose, ethyl cellulose, CMC, hydroxy ethyl cellulose, hydroxypropyl cellulose, PVA, PVM, PVP, sodium polyacrylate, carboxy vinyl polymer, locust bean gum, guar gum, tamarind gum, cellulose dialkyl dimethylammonium sulfate, xanthan gum, aluminum magnesium silicate, bentonite, hectorite, AlMg silicate (beagum), laponite, and silicic acid anhydride.

Examples of the ultraviolet light absorbents include: benzoic acid ultraviolet light absorbents (for example, paraminobenzoic acid (hereafter abbreviated as PABA), PABA monoglycerin ester, N, N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester; anthranilic acid ultraviolet light absorbents (for example, homo mentyl-N-acetyl anthranilate); salicylic acid ultraviolet light absorbents (for example, amyl salicylate, mentyl salicylate, homo mentyl salicylate, octyl salicylate, phenyl salicylate, benzil salicylate, and p-isopropanol phenyl salicylate); cinnamic acid ultraviolet light absorbents (for example, octylcinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxycinnamate, ethyl-α-cyano-βphenylcinnamate, 2-ethylhexyl-α-cyano-β-phenylcinnamate, and glyceryl mono-2-ethyl hexanoyl-diparamethoxycinnamate); benzophenone ultraviolet light absorbents (for example, 2,4-dihydroxybenzophenone, 2,2'-dihydroxy-4-methoxybenzophenone, 2,2'-dihydroxy-4,4'-dimethoxybenzophenone, 2,2', 4,4'-tetrahydroxybenzophenone, 2-hydroxy-4-methoxybenzophenone, 2-hydroxy-4-methoxy-4'-methylbenzophenone, 2-hydorxy-4-methoxybenzophenone-5-sulfonate, 4-phenyl benzophenone, 2-ethylhexyl-4'-phenyl-benzophenone-2-carboxylate, 2-hydroxy-4-n-octoxybenzophenone, and 4-hydroxy-3-carboxybenzophenone); 3-(4'-methylbenzylidene)-d, l-camphor and 3-benzylidene-d, l-camphor; 2-phenyl-5-methyl benzoxazol; 2,2'-hydroxy-5-methylphenyl benzotriazol; 2-(2'-hydroxy-5'-t-octylphenyl) benzotriazol; 2-(2'-hydroxy-5'-methylphenyl benzotriazol;) dibenzaladine; dianisoylmethane; 4-methoxy-4'-t-butyl dibenzoyl-methane; and 5-(3,3-dimethyl-2-norbornylidene)-3-pentane-2-one.

Examples of the sequestering agents include: 1-hydroxy ethane-1,1-diphosphonic acid, 1-hydroxy ethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, and trisodium ethylenediaminehydroxyethyl triacetate.

Examples of the lower alcohols include ethanol, propanol, isopropanol, isobutanol, and tert-butyl alcohol.

Examples of the polyhydric alcohols include: dihydric alcohols (for example, ethylene glycol, propylene glycol, trimethylene glycol, 1,2-butylene glycol, 1,3-butylene glycol, tetramethylene glycol, 2,3-butylene glycol, pentam-ethylene glycol, 2-butene-1,4-diol, hexylene glycol, and octylene glycol); trihydric alcohols (for example, glycerin and trimethylolpropane); tetrahydric alcohols (for example, pentaerythritol such as 1,2,6-hexanetriol); pentahydric alcohols (for example, xylitol); hexahydric alcohols (for example, sorbitol, mannitol); polyhydric alcohol polymers (for example, diethylene glycol, dipropylene glycol, triethylene glycol, polypropylene glycol, tetraethylene glycol, diglycerin, polyethylene glycol, triglycerin, tetraglycerin, and polyglycerin); dihydric alcohol alkylethers (for example, ethylene glycol monomethyl ether, ethylene glycol monoethyl ether, ethylene glycol monobutyl ether, ethylene glycol monophenyl ether, ethylene glycol monohexyl ether, ethylene glycol mono 2-methyl hexyl ether, ethylene glycol isoamyl ether, ethylene glycol benzyl ether, ethylene glycol isopropyl ether, ethylene glycol dimethylether, ethylene glycol diethyl ether, and ethylene glycol dibutyl ether); dihydric alcohol alkylethers (for example, diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycolmonomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (for example, ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycolmonomethyl ether acetate, propylene glycol monoethyl ether acetate, propylene glycol monopropyl ether acetate, and propylene glycol monophenyl ether acetate); glycerin mono alkyl ethers (for example, ichthammol, selachyl alcohol, and batyl alcohol); Sugar alcohols (for example, sorbitol, maltitol, maltotriose, mannitol, sucrose, erythritol, glucose, fructose, starch amylolysis sugar, maltose, xylitose, and alcohol prepared by the reduction of starch amylolysis sugar); glysolid; tetrahydro furfuryl alcohol; POE-tetrahydro furfuryl alcohol; POP-butyl ether; POP/POE-butyl ether; Tripoli oxypropylene glycerin ether; POP-glycerin ether; POP-glycerin ether phosphoric acid; POP/POE-pentane erythritol ether, and polyglycerin.

Examples of the monosaccharides include: trioses (for example, D-glyceryl aldehyde and dihydroxyacetone); tetrose (for example, D-etythrose, D-erythrulose, D-threose, and erythritol); pentose (for example, L-arabinose, D-xylose, L-lyxose, D-arabinose, D-ribose, D-ribulose, D-xylulose, and L-xylulose); Hexose (for example, D-glucose, D-talose, D-psicose, D-galactose, D-fructose, L-galactose, L-mannose, and D-tagatose); heptose (for example, aldoheptose and heprose); octose (for example, octurose); deoxysugar (for example, 2-deoxy-D-ribose, 6-deoxy-L-galactose, and 6-deoxy-L-mannose); amino sugar (for example, D-glucosamine, D-galactosamine, sialic acid, amino uronic acid, and muramic acid); and uronic acid (for example, D-glucuronic acid, D-mannuronic acid, L-guluronic acid, D-galacturonic acid, and L-iduronic acid).

Examples of the oligosaccharides include sucrose, gentianose, umbelliferose, lactose, planteose, isolignoses, α,α-trehalose, raffinose, lignoses, umbilicine, stachyose and verbascose.

Examples of the polysaccharides include cellulose, quince seed, chondroitin sulfate, starch, galactan, dermatan sulfate, glycogen, gum arabic, heparan sulfate, hyaluronic acid, traganth gum, keratan sulfate, chondroitin, xanthan gum, mucoitin sulfuric acid, guar gum, dextran, kerato sulfate, locust bean gum, succinoglucan, and charonic acid.

Examples of the amino acids include neutral amino acid (for example, threonine and cysteine) and basic amino acid (for example, hydroxylysine). Examples of the amino acid derivatives include sodium acyl sarcosinate (sodium N-lauroyl sarcosinate), acyl glutamate, acyl β-sodium alanine, glutathione, and pyrrolidone carboxylic acid.

Examples of the organic amines include monoethanolamine, diethanolamine, triethanolamine, morpholine, triisopropanolamine, 2-amino-2-carbinyl-1,3-propanediol, and 2-amino-2-carbinyl-1-propanol.

Examples of the high polymer emulsions include acrylic resin emulsion, ethyl polyacrylate emulsion, acryl resin liquid, polyacrylic alkyl ester emulsion, polyvinyl acetate resin emulsion, and natural rubber latex.

Examples of the pH adjustment agents include buffers such as lactic acid-sodium lactate, citric acid-sodium citrate, and succinic acid-sodium succinate.

Examples of the vitamins include vitamin A, B1, B2, B6, C and E as well as their derivatives, pantothenic acid and its derivatives, and biotin.

Examples of the antioxidants include tocopherols, dibutyl hydroxytoluene, butyl hydroxyanisole, and gallic ester.

Examples of the antioxidation auxiliary agents include phosphoric acid, citric acid, ascorbic acid, maleic acid, malonic acid, succinic acid, fumaric acid, cephalin, hexametaphosphate, phytic acid, and ethylene diamine tetraacetic acid.

Examples of other possible ingredients include antiseptics (ethylparaben and butylparaben); anti-inflammatory agents (for example, glycyrrhizic acid derivatives, glycyrrhetinic acid derivatives, salicylic acid derivatives, hinokitiol, zinc oxide, and allantoin); whitening agents (for example, placenta extract and creeping saxifrage extract); various extracts (for example, phellodendron bark, goldthread, lithospermum root, *Paeonia lactiflora*, *Swertia japonica*, Birch, sage, loquat, carrot, aloe, *Malva sylvestris*, Iris, grape, coix, sponge gourd, lily, saffron, *Cnidium officinale*, ginger, *Hypericum erectum*, Ononis, garlic, Guinea pepper, citrus unshiu peel, *Ligusticum acutilobum*, and seaweed), activators (royal jelly, photosensitive substances, and cholesterol derivatives); blood circulation promoting agents (for example, nonylic acid vanillylamide, nicotinic acid benzyl esters, nicotinic acid β-butoxy ethyl esters, capsaicin, zingerone, cantharis tincture, ichthammol, tannic acid, α-borneol, tocopherol nicotinate, inositol hexanicotinate, cyclandelate, cinnarizine, tolazoline, acetylcholine, verapamil, cepharanthine, and γ-orizanol); anti-seborrhea agents (for example, sulfur and thiantol); and antiinflammatory agents (for example, tranexamic acid, thiotaurine, and hypotaurine).

Any formulation can be used including the solution type, the solubilized type, powder dispersion type, water-oil bilayer type, and water-oil-powder three layer type. The product form of the endermic liniment of the present invention is arbitrary. It can be used in lotions, emulsion, cream, facial cosmetics such as packs; makeup cosmetics such as foundations, lip sticks, eye shadow; body cosmetics; aroma cosmetics; skin cleaners such as makeup removers and body shampoos; and ointment.

As for applications of the present invention, a polyoxyethylene dicarboxylate represented by the aforementioned chemical formula (1) (particularly diethoxyethyl succinate) can be blended in publicly known existing products including hair cleaners such as shampoo and rinse; hair cosmetics such as hair dressing (styling agents); and bath additives to obtain marketable products. These product can be prepared with a conventional method by blending one, two or more of the optional ingredients composing each product (optional ingredients of the endermic liniment enumerated as above) and a polyoxyethylene dicarboxylate (particularly diethoxyethyl succinate).

EXAMPLES

The present invention is described below by referring to Examples. The present invention is not limited by Examples. The blend ratios are in wt % units. First, the testing method and evaluation method used in Examples and Comparative examples are described below.

"Test Method Using Conductance Measurements"

The forearms of a panel of ten people were used. Skin conductance was measured before application and 30 minutes, 60 minutes, and 120 minutes after application. The moisture retaining effect was evaluated based on the ratio of change. The ratio of change in the skin conductance is obtained by the following equation (1). It enables evaluation of the effect on water absorption of the horny cell layer. A small ratio of change means an increase in the moisture in the horny cell layer, indicating a high moisture retaining effect.

Equation 1

Conductance change ratio=(Conductance before application)/(Conductance after application)

The evaluation criteria of the "Test method using conductance measurements" are as follows:

⊚ . . . Average conductance change ratio of 10 panelists: 0 or more and less than 0.1

○ . . . Average conductance change ratio of 10 panelists: 0.1 or more and less than 0.2

Δ . . . A Average conductance change ratio of 10 panelists: 0.2 or more and less than 0.5

X . . . Average conductance change ratio of 10 panelists: 0.5 or more

"Evaluation (1): Quickness of Absorption into the Skin"

Quickness of absorption into the skin during use was evaluated by an actual use test by a panel of 10 specialists. The evaluation criteria are as follows:

⊚ . . . 8 or more specialists in the panel acknowledged adequate quickness of absorption into the skin during use.

○ . . . 6 or more and less than 8 specialists in the panel acknowledged adequate quickness of absorption into the skin during use.

Δ . . . 3 or more and less than 6 specialists in the panel acknowledged adequate quickness of absorption into the skin during use.

X . . . Less than 3 specialists in the panel acknowledged adequate quickness of absorption into the skin during use.

"Evaluation (2): Smoothness of the Skin"

Smoothness of the skin during and after use was evaluated by an actual use test by a panel of 10 specialists. The evaluation criteria are as follows:

⊚ . . . 8 or more specialists in the panel acknowledged smooth skin during and after use.

○ . . . 6 or more and less than 8 specialists in the panel acknowledged smooth skin during and after use.

Δ . . . 3 or more and less than 6 specialists in the panel acknowledged smooth skin during and after use.

X . . . Less than 3 specialists in the panel acknowledged smooth skin during and after use.

"Evaluation (3): Non-stickiness of the Skin"

Non-stickiness of the skin during and after use was evaluated by an actual use test by a panel of 10 specialists. The evaluation criteria are as follows:

⊚ . . . 8 or more specialists in the panel acknowledged non-stickiness of the skin during and after use.

○ . . . 6 or more and less than 8 specialists in the panel acknowledged non-stickiness of the skin during and after use.

Δ . . . 3 or more and less than 6 specialists in the panel acknowledged non-stickiness of the skin during and after use.

X . . . Less than 3 specialists in the panel acknowledged non-stickiness of the skin during and after use.

"Evaluation (4): Perceived Moisture Retaining Effect"

The perceived moisture retaining effect 120 minutes after use was evaluated by an actual use test by a panel of 10 specialists. The evaluation criteria are as follows:

⊚ . . . 8 or more specialists in the panel perceived a moisture retaining effect.

○ . . . 6 or more and less than 8 specialists in the panel perceived a moisture retaining effect.

Δ . . . 3 or more and less than 6 specialists in the panel perceived a moisture retaining effect.

X . . . Less than 3 specialists in the panel perceived a moisture retaining effect.

"Examples 1–10 and Comparative Examples 1–6"

For Examples 1–2 and Comparative examples 1–3 prepared according to the blend ratios listed in Table 1–1, the conductance change ratio was measured. Endermic liniments (lotion) of Examples 3–10 and Comparative examples 4–6 were prepared with a conventional method according to the blend ratios listed in Table 2 and 3, and evaluation testing was conducted according to the aforementioned evaluations (1), (2), (3), and (4). The results are shown in each table.

TABLE 1-1

|  |  |  | Conductance change ratio | | |
|---|---|---|---|---|---|
|  |  |  | 30 minutes | 60 minutes | 120 minutes |
| Examples | 1 | 3% diethoxyethyl succinate + 7% glycerin aqueous solution | ⊚ | ⊚ | ⊚ |
|  | 2 | 3% diethoxyethyl succinate +7% 1,3-butylene glycol aqueous solution | ⊚ | ⊚ | ⊚ |
| Comparative example | 1 | Ion-exchange water | X | X | X |
|  | 2 | 10% aqueous solution of 1,3-butylene glycol | Δ | Δ | Δ |
|  | 3 | 10% aqueous solution of glycerin | ○ | ○ | Δ |

Table 1–1 indicates that an aqueous solution (lotion) containing a polyoxyethylene dicarboxylate (diethoxyethyl succinate) shows a synergistic increase in the moisture retaining effect when combined with a humectant.

TABLE 1-2

| | Examples | | | |
|---|---|---|---|---|
| Ingredient | 3 | 4 | 5 | 6 |
| Ethanol | 10 | 10 | 10 | 10 |
| Glycerin | 5 | 5 | 5 | 5 |
| 1,3 butylene glycol | 5 | 5 | 5 | 5 |
| Diethoxyethyl succinate | 0.001 | 0.1 | 5.0 | 10.0 |
| Nicotinamide | 0.3 | 0.3 | 0.3 | 0.3 |
| Sodium pyrrolidone carboxylate | 0.5 | 0.5 | 0.5 | 0.5 |
| Purified water | Balance | Balance | Balance | Balance |
| "Evaluation (1): Quickness of absorption into the skin" | ○ | ⊚ | ⊚ | ⊚ |
| "Evaluation (2): Smoothness of skin" | ○ | ⊚ | ⊚ | ⊚ |
| "Evaluation (3): Non-stickiness to the skin" | ○ | ⊚ | ⊚ | ⊚ |
| "Evaluation (4): Perceived moisture retaining effect" | ○ | ⊚ | ⊚ | ⊚ |

TABLE 1-3

| | Examples | | | |
|---|---|---|---|---|
| Ingredient | 7 | 8 | 9 | 10 |
| Ethanol | 10 | 10 | 10 | 10 |
| Glycerin | 5 | 5 | 5 | 5 |
| 1,3 butylene glycol | 5 | 5 | 5 | 5 |
| Diethyl carbitol sebacate | 0.1 | 5.0 | — | — |
| Diethoxyethyl succinate | — | — | 0.1 | 5.0 |
| Nicotinamide | 0.3 | 0.3 | 0.3 | 0.3 |
| Sodium pyrrolidone carboxylate | 0.5 | 0.5 | 0.5 | 0.5 |
| Purified water | Balance | Balance | Balance | Balance |
| "Evaluation (1): Quickness of absorption into the skin" | ⊚ | ⊚ | ⊚ | ⊚ |
| "Evaluation (2): Smoothness of skin" | ○ | ⊚ | ○ | ⊚ |
| "Evaluation (3): Non-stickiness to the skin" | ○ | ⊚ | ○ | ⊚ |
| "Evaluation (4): Perceived moisture retaining effect" | ○ | ⊚ | ○ | ⊚ |

TABLE 1-4

| | Comparative examples | | |
|---|---|---|---|
| Ingredients | 4 | 5 | 6 |
| Ethanol | 10 | 10 | 10 |
| Glycerin | 5 | 10 | — |
| 1,3 butylene glycol | 5 | — | 10 |
| Diethoxyethyl succinate | — | — | — |
| Nicotinamide | 0.3 | 0.3 | 0.3 |
| Sodium pyrrolidone carboxylate | 0.5 | 0.5 | 0.5 |
| Purified water | Balance | Balance | Balance |
| "Evaluation (1): Quickness of absorption into the skin" | X | X | X |
| "Evaluation (2): Smoothness of skin" | ○ | ○ | ○ |

TABLE 1-4-continued

|  | Comparative examples | | |
|---|---|---|---|
| Ingredients | 4 | 5 | 6 |
| "Evaluation (3): Non-stickiness to the skin" | X | X | Δ |
| "Evaluation (4): Perceived moisture retaining effect" | Δ | Δ | Δ |

The aforementioned results indicate that the endermic liniment of the present invention has superior effects according to all the evaluation items. Other Examples of the present invention are listed below.

Example 11

Cream

| A. Oil phase | |
|---|---|
| Stearic acid | 10.0 wt % |
| Stearyl alcohol | 4.0 |
| Butyl stearate | 8.0 |
| Stearic acid monoglycerin ester | 2.0 |
| Vitamin E acetate | 0.5 |
| Vitamin A palmitate | 0.1 |
| Diethoxyethyl succinate | 5.0 |
| Macadamia nut oil | 1.0 |
| Tea seed oil | 3.0 |
| Perfume | 0.4 |
| Preservatives | Appropriate amount |
| B. Water phase | |
| Glycerin | 4.0 |
| 1,2 pentane diol | 3.0 |
| Sodium hyaluronate | 1.0 |
| Potassium hydroxide | 2.0 |
| Magnesium ascorbate phosphate | 0.1 |
| L-arginine hydrochloride | 0.01 |
| Trisodium edetate | 0.05 |
| Purified water | Balance |

(Preparation Method and Evaluation)

Oil phase A and water phase B were separately heated up to 70° C. and dissolved completely. Phase A was added to phase B and emulsified with an emulsifier. The emulsion was cooled with a heat exchanger to obtain a cream. The obtained cream had superior smoothness without a sticky sensation and also had a lasting moisture retaining effect.

Example 12

Cream

| A. Oil phase | |
|---|---|
| Cetanol | 4.0 wt % |
| Petrolatum | 7.0 |
| Isopropyl myristate | 8.0 |
| Squalane | 15.0 |
| Stearic acid monoglycerin ester | 2.2 |
| POE (20) sorbitan monostearate | 2.8 |
| Diethoxyethyl succinate | 10.0 |
| Vitamin E nicotinate | 2.0 |
| Perfume | 0.3 |
| Antioxidant | Appropriate amount |
| Preservative | Appropriate amount |
| B. Water phase | |
| Glycerin | 10.0 |
| Sodium hyaluronate | 0.02 |
| Propylene glycol 1 | 4.0 |
| Sodium pyrrolidone carboxylate | 1.0 |
| Disodium edetate | 0.01 |
| Purified water | Balance |

(Preparation Method and Evaluation)

A cream was obtained in the same manner as in Example 11. The obtained cream had superior smoothness without a sticky sensation and also had a lasting moisture retaining effect.

Example 13

Emulsion

| A. Oil phase | |
|---|---|
| Squalane | 5.0 wt % |
| Oleyl oleate | 3.0 |
| Petrolatum | 2.0 |
| Sorbitan sesquioleic ester | 0.8 |
| Polyoxyethylene oleyl ether (20E0) | 1.2 |
| Diethoxyethyl succinate | 8.0 |
| Evening primrose oil | 0.5 |
| Perfume | 0.3 |
| Preservative | Appropriate amount |
| B. Water phase | |
| 1,3 butylene glycol | 4.5 |
| Ethanol | 3.0 |
| Carboxy vinyl polymer | 0.2 |
| Potassium hydroxide | 0.1 |
| L-arginine L-aspartate | 0.01 |
| Edetate | 0.05 |
| Purified water | Balance |

(Preparation Method and Evaluation)

An emulsion was obtained in the same manner as in Example 11. The obtained emulsion had superior smoothness without a sticky sensation and also had a lasting moisture retaining effect.

Example 14

Foundation

| A. Oil phase | |
|---|---|
| Cetanol | 3.5 wt % |
| Deodorized lanolin | 4.0 |
| Jojoba oil | 5.0 |
| Petrolatum | 2.0 |
| Squalane | 6.0 |
| Stearic acid monoglycerin ester | 2.5 |
| POE (60) hydrogenated castor oil | 1.5 |
| POE (20) cetyl ether | 1.0 |
| Diethoxyethyl succinate | 2.0 |
| Pyridoxine tripalmitate | 0.1 |
| Preservative | Appropriate amount |
| Perfume | 0.3 |

-continued

| B. Water phase | |
|---|---|
| Propylene glycol | 10.0 |
| Ready-mixed powder | 12.0 |
| Trisodium ethylenediamine hydroxyethyl triacetate | 1.0 |
| Purified water | Balance |

(Preparation Method and Evaluation)

A foundation was obtained in the same manner as in Example 11. The obtained foundation had superior smoothness without a sticky sensation and also had a lasting moisture effect.

Example 15

Lotion

| A. Alcohol phase | |
|---|---|
| Ethanol | 5.0 wt % |
| POE oleyl alcohol ether | 2.0 |
| Diethoxyethyl succinate | 3.0 |
| 2-ethylhexyl-P-dimethyl amino benzoate | 0.18 |
| Perfume | 0.05 |
| B. Water phase | |
| 1,3 butylene glycol | 9.5 |
| Sodium pyrrolidone carboxylate | 0.5 |
| Nicotinamide | 0.3 |
| Glycerin | 5.0 |
| Purified water | Balance |

(Preparation Method and Evaluation)

Alcohol phase A was added to water phase B and solubilized to obtain a lotion. The obtained lotion had superior smoothness without a sticky sensation and also had a lasting moisture retaining effect.

"Evaluation (1): Quickness of Absorption into the Skin"

Quickness of absorption into the skin during use was evaluated by an actual use test by a panel of 10 specialists. The evaluation criteria are as follows:

⊚ . . . 8 or more specialists in the panel acknowledged adequate quickness of absorption into the skin during use.

○ . . . 6 or more and less than 8 specialists in the panel acknowledged adequate quickness of absorption into the skin during use.

Δ . . . 3 or more and less than 6 specialists in the panel acknowledged adequate quickness of absorption into the skin during use.

X . . . Less than 3 specialists in the panel acknowledged adequate quickness of absorption into the skin during use.

"Evaluation (2): Smoothness of the Skin"

Smoothness of the skin during and after use was evaluated by an actual use test by a panel of 10 specialists. The evaluation criteria are as follows:

⊚ . . . 8 or more specialists in the panel acknowledged smooth skin during and after use.

○ . . . 6 or more and less than 8 specialists in the panel acknowledged smooth skin during and after use.

Δ . . . 3 or more and less than 6 specialists in the panel acknowledged smooth skin during and after use.

X . . . Less than 3 specialists in the panel acknowledged smooth skin during and after use.

"Evaluation (3): Non-Stickiness to the Skin"

Non-stickiness of the skin during and after use was evaluated by an actual use test by a panel of 10 specialists. The evaluation criteria are as follows:

⊚ . . . 8 or more specialists in the panel acknowledged non-stickiness of the skin during and after use.

○ . . . 6 or more and less than 8 specialists in the panel acknowledged non-stickiness of the skin during and after use.

Δ . . . 3 or more and less than 6 specialists in the panel acknowledged non-stickiness of the skin during and after use.

X . . . Less than 3 specialists specialists in the panel acknowledged non-stickiness of the skin during and after use.

"Evaluation (4): Whitening Effect Test by Means of Accumulation and Such"

A group of ten subjects who suffered from a dark complexion, skin stains, freckles, etc. applied the samples on their faces daily for three months. After the three months, the whitening effect was evaluated. The evaluation criteria are as follows:

⊚ . . . 8 or more specialists in the panel acknowledged that the pigment deposition hardly showed.

○ . . . 6 or more and less than 8 specialists in the panel acknowledged that the pigment deposition hardly showed.

Δ . . . 3 or more and less than 6 specialists in the panel acknowledged that the pigment deposition hardly showed.

X . . . Less than 3 specialists in the panel acknowledged that the pigment deposition hardly showed.

"Examples 1–8 and Comparative Examples 1–3"

Endermic liniments (lotion) of Examples 1–8 and Comparative examples 1–3 were prepared with a conventional method according to the blend ratios listed in Tables 2–1 to 2–3, and the evaluation testing was conducted according to the aforementioned evaluations (1), (2), (3), and (4). The results are shown in each table.

TABLE 2-1

| | Examples | | | |
|---|---|---|---|---|
| An ingredient | 1 | 2 | 3 | 4 |
| Ethanol | 5 | 5 | 5 | 5 |
| Glycerin | 3 | 3 | 3 | 3 |
| 1,3 butylene glycol | 5 | 5 | 5 | 5 |
| Diethoxyethyl succinate | 0.001 | 0.1 | 5.0 | 10.0 |
| Nicotinamide | 0.3 | 0.3 | 0.3 | 0.3 |
| Sodium pyrrolidone carboxylate | 0.5 | 0.5 | 0.5 | 0.5 |
| Hydroquinone α -D-glucose | 0.01 | 0.1 | 5.0 | 10.0 |
| Methylparaben | 0.1 | 0.1 | 0.1 | 0.1 |
| Succinic acid | 0.1 | 0.1 | 0.1 | 0.1 |
| Sodium succinate | 0.9 | 0.9 | 0.9 | 0.9 |
| Purified water | Balance | Balance | Balance | Balance |
| "Evaluation (1): Quickness of absorption into the skin" | ○ | ⊚ | ⊚ | ⊚ |
| "Evaluation (2): Smoothness of the skin" | ○ | ⊚ | ⊚ | ⊚ |
| "Evaluation (3): Non-stickiness of the skin" | ○ | ⊚ | ⊚ | ⊚ |
| Evaluation (4) whitening effect | ○ | ○ | ○ | ○ |

TABLE 2-2

| An ingredient | Examples 5 | 6 | 7 | 8 |
|---|---|---|---|---|
| Ethanol | 5 | 5 | 5 | 5 |
| Glycerin | 3 | 3 | 3 | 3 |
| 1,3 butylene glycol | 5 | 5 | 5 | 5 |
| Diethyl carbitol sebacate | 0.1 | 5.0 | — | — |
| Diethoxyethyl succinate | — | — | 0.1 | 5.0 |
| Nicotinamide | 0.3 | 0.3 | 0.3 | 0.3 |
| Sodium pyrrolidone carboxylate | 0.5 | 0.5 | 0.5 | 0.5 |
| Hydroquinone α -D-glucose | 2.0 | 2.0 | 2.0 | 2.0 |
| Methylparaben | 0.1 | 0.1 | 0.1 | 0.1 |
| Succinic acid | 0.1 | 0.1 | 0.1 | 0.1 |
| Sodium succinate | 0.9 | 0.9 | 0.9 | 0.9 |
| Purified water | Balance | Balance | Balance | Balance |
| "Evaluation (1): Quickness of absorption into the skin" | ◎ | ◎ | ◎ | ◎ |
| "Evaluation (2): Smoothness of the skin" | ○ | ◎ | ○ | ◎ |
| "Evaluation (3): Non-stickiness of the skin" | ○ | ◎ | ○ | ◎ |
| An ingredient | ○ | ○ | ○ | ○ |

TABLE 2-3

| An ingredient | Comparative example 1 | 2 | 3 |
|---|---|---|---|
| Ethanol | 5 | 5 | 5 |
| Glycerin | 3 | 8 | — |
| 1,3 butylene glycol | 5 | — | 8 |
| Diethoxyethyl succinate | — | — | — |
| Nicotinamide | 0.3 | 0.3 | 0.3 |
| Sodium pyrrolidone carboxylate | 0.5 | 0.5 | 0.5 |
| Hydroquinone α -D-glucose | 2.0 | 5.0 | 10.0 |
| Methylparaben | 0.1 | 0.1 | 0.1 |
| Succinic acid | 0.1 | 0.1 | 0.1 |
| Sodium succinate | 0.9 | 0.9 | 0.9 |
| Purified water | Balance | Balance | Balance |
| "Evaluation (1): Quickness of absorption into the skin" | X | X | X |
| "Evaluation (2): Smoothness of the skin" | ○ | Δ | ○ |
| "Evaluation (3): Non-stickiness of the skin" | X | X | X |
| Evaluation (4) whitening effect | ○ | ○ | ○ |

The aforementioned results indicate that the endermic liniment of the present invention has superior effects according to all the evaluation items. Other Examples of the present invention are listed below.

Example 9

Cream

| A. Oil phase | |
|---|---|
| Stearic acid | 10.0 mass % |
| Stearyl alcohol | 4.0 |
| Butyl stearate | 8.0 |
| Stearic acid monoglycerin ester | 2.0 |
| Vitamin E acetate | 0.5 |
| Vitamin A palmitate | 0.1 |
| Diethoxyethyl succinate | 5.0 |
| Macadamia nut oil | 1.0 |
| Tea seed oil | 3.0 |
| Perfume | 0.4 |
| Preservative | Appropriate amount |

| B. Water phase | |
|---|---|
| Glycerin | 4.0 |
| 1,2 pentane diol | 3.0 |
| Sodium hyaluronate | 1.0 |
| Potassium hydroxide | 2.0 |
| L-ascorbyl-2-phosphoric ester | 2.0 |
| L-arginine hydrochloride | 0.01 |
| Trisodium edetate | 0.05 |
| Succinic acid | 0.1 |
| Sodium succinate | 0.9 |
| Purified water | Balance |

(Preparation Method and Evaluation)

Oil phase A and water phase B were separately heated up to 70° C. and dissolved completely. Phase A was added to phase B and emulsified with an emulsifier. The emulsion was cooled with a heat exchanger to obtain a cream. The obtained cream had superior smoothness without a sticky sensation while maintaining the whitening effect.

Example 10

Cream

| A. Oil phase | |
|---|---|
| Cetanol | 4.0 mass % |
| Petrolatum | 7.0 |
| Isopropyl myristate | 8.0 |
| Squalane | 15.0 |
| Stearic acid monoglycerin ester | 2.2 |
| POE (20) sorbitan monostearate | 2.8 |
| Diethoxyethyl succinate | 10.0 |
| Vitamin E nicotinate | 2.0 |
| Perfume | 0.3 |
| Antioxidant | Appropriate amount |
| Preservative | Appropriate amount |

| B. Water phase | |
|---|---|
| Glycerin | 10.0 |
| Sodium hyaluronate | 0.02 |
| Dipropylene glycol | 4.0 |
| L-ascorbyl-2-sulfuric ester | 1.0 |
| Sodium pyrrolidone carboxylate | 1.0 |
| Disodium edetate | 0.01 |
| Succinic acid | 0.1 |
| Sodium succinate | 0.9 |
| Purified water | Balance |

(Preparation Method and Evaluation)

A cream was obtained in the same manner as in Example 9. The obtained cream had superior smoothness without a sticky sensation while maintaining the whitening effect.

Example 11

Emulsion

| A. Oil phase | |
|---|---|
| Squalane | 5.0 mass % |
| Oleyl oleate | 3.0 |
| Petrolatum | 2.0 |
| Sorbitan ester sesquioleate | 0.8 |
| Polyoxyethylene oleyl ether (20EO) | 1.2 |
| Diethoxyethyl succinate | 8.0 |

-continued

| | |
|---|---|
| Evening primrose oil | 0.5 |
| Perfume | 0.3 |
| Preservative | Appropriate amount |
| B. Water phase | |
| 1,3 butylene glycol | 4.5 |
| Ethanol | 3.0 |
| Carboxy vinyl polymer | 0.2 |
| Potassium hydroxide | 0.1 |
| Kojic acid | 5.0 |
| L-arginine L-aspartate | 0.01 |
| Edetate | 0.05 |
| Succinic acid | 0.1 |
| Sodium succinate | 0.9 |
| Purified water | Balance |

(Preparation Method and Evaluation)

An emulsion was obtained in the same manner as in Example 9. The obtained emulsion had superior smoothness without a sticky sensation while maintaining the whitening effect.

Example 12

Foundation

| A. Oil phase | |
|---|---|
| Cetanol | 3.5 mass % |
| Deodorized lanolin | 4.0 |
| Jojoba oil | 5.0 |
| Petrolatum | 2.0 |
| Squalane | 6.0 |
| Stearic acid monoglycerin ester | 2.5 |
| POE (60) hydrogenated castor oil | 1.5 |
| POE (20) cetyl ether | 1.0 |
| Diethoxyethyl succinate | 2.0 |
| Pyridoxine tripalmitate | 0.1 |
| Preservative | Appropriate amount |
| Perfume | 0.3 |
| B. Water phase | |
| Propylene glycol | 10.0 |
| Hydroquinone α -D-glucose | 4.0 |
| Ready-mixed powder | 12.0 |
| Trisodium ethylenediamine hydroxyethyl triacetate | 1.0 |
| Purified water | Balance |

(Preparation Method and Evaluation)

Foundation was obtained in the same manner as in Example 9. The obtained foundation had superior smoothness without a sticky sensation while maintaining the whitening effect.

Example 13

Lotion

| A. Alcohol phase | |
|---|---|
| Ethanol | 5.0 mass % |
| POE oleyl alcohol ether | 2.0 |
| Diethoxyethyl succinate | 3.0 |
| 2-ethylhexyl-P-dimethyl amino benzoate | 0.18 |
| Perfume | 0.05 |

-continued

| | |
|---|---|
| B. Water phase | |
| 1,3 butylene glycol | 9.5 |
| Sodium pyrrolidone carboxylate | 0.5 |
| Nicotinamide | 0.3 |
| Glycerin | 5.0 |
| L-ascorbyl palmitate | 1.0 |
| Succinic acid | 0.1 |
| Sodium succinate | 0.9 |
| Purified water | Balance |

(Preparation Method and Evaluation)

Alcohol phase A was added to water phase B and solubilized to obtain a lotion. The obtained lotion had superior smoothness without a sticky sensation while maintaining the whitening effect.

INDUSTRIAL APPLICABILITY

The endermic liniment of the present invention achieves a superior tactile sensation during use, smoothness in particular, without a sticky sensation, while maintaining a lasting moisture effect by means of blending in a humectant and a polyoxyethylene dicarboxylate.

The present invention can provide an endermic liniment that is superior in terms of the tactile sensation during use, smoothness in particular, and without a sticky sensation while maintaining the whitening effect.

What is claimed is:

1. An endermic liniment consisting essentially of a polyoxyethylene dicarboxylate represented by the following chemical formula (1),

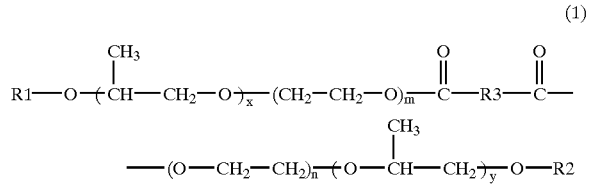

(1)

wherein R1 and R2 are hydrogen or alkyl or branched alkyl groups having 1–4 carbon atoms, and m, n, X, and Y are integers 0–5 which are not all zero at the same time, R3 is a branched or linear chain alkylene group having 0–10 carbon atoms, and a humectant, wherein the polyoxyethylene dicarboxylate is diethoxy ethyl succinate.

2. The endermic liniment of claim 1, wherein the humectant is selected from the group consisting of polyethylene glycol, propylene glycol, glycerin, 1,3-butylene glycol, xylitol, sorbitol, maltitol, chondroitin sulfate, hyaluronic acid, inucoitin sulfuric acid, charonic acid, atelocollagen, cholesteryl-12-hydroxy stearate, sodium lactate, bile salt, di-pyrrolidone carboxylic acid salt, short chain soluble collagen, diglycerin (EO)PO adduct, chestnut rose extract, yarrow extract, and sweet clover extract.

3. An endermic liniment consisting essentially of:

diethoxy ethyl succinate;

a humectant selected from the group consisting of polyethylene glycol, propylene glycol, glycerin, 1,3-butylene glycol, xylitol, sorbitol, maltitol, chondroitin sulfate, hyaluronic acid, mucoitin sulfuric acid, charonic acid, atelocollagen, cholesteryl-12-hydroxy stearate, sodium lactate, bile salt, di-pyrrolidone carboxylic acid salt, short chain soluble collagen, diglycerin (EO)PO adduct, chestnut rose extract, yarrow extract, and sweet clover extract; and one or more whitening agents selected from the group consisting of L-ascorbic acid, L-ascorbyl alkyl ester, L-ascorbyl phosphate, L-ascorbyl sulfate, alkali metal salts thereof, alkaline earth metal salts thereof, kojic acid, kojic esters, kojic ethers, a glucoside of hydroquinone, hexose glucosides, pentose glucosides, amino acid glucosides, uronic acid glucosides, esters of uronic acid glucosides, and ethers of uronic acid glucosides.

* * * * *